US00PP30471P3

(12) United States Plant Patent
Olesen

(10) Patent No.: US PP30,471 P3
(45) Date of Patent: May 7, 2019

(54) CLIMBING ROSE PLANT NAMED 'POULCY034'

(50) Latin Name: ***Rosa* hybrid**
Varietal Denomination: Poulcy034

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 18 days.

(21) Appl. No.: 15/731,984

(22) Filed: Sep. 5, 2017

(65) Prior Publication Data

US 2019/0075693 P1 Mar. 7, 2019

(51) Int. Cl.
*A01H 5/02* (2018.01)

(52) U.S. Cl.
USPC ..... Plt./114
CPC ..... *A01H 5/02* (2013.01)

(58) Field of Classification Search
USPC ..... Plt./114
See application file for complete search history.

(56) References Cited

PUBLICATIONS

UPOV hit for climbing rose plant named 'Poulcy034', QZ PBR 48859, filed Sep. 19, 2016.*

* cited by examiner

*Primary Examiner* — Anne Marie Grunberg

(57) ABSTRACT

A new garden rose plant of the climbing class which has abundant, pink flowers and attractive foliage. This new and distinct variety has shown to be uniform and stable in the resulting generations from asexual propagation.

3 Drawing Sheets

Botanical designation: *Rosa* hybrid.
Variety denomination: 'Poulcy034'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2006 and the resulting seeds were planted in a controlled environment in Fredensborg, Denmark. The new variety, named 'Poulcy034', originated as a single seedling from the stated cross.

The new variety may be distinguished from its male pollen parent and female seed parent primarily by the following characteristics. The male pollen parent plant has orange red flowers while the new variety has pink flowers. The female seed parent is a grandiflora rose, while the newly claimed plant is a climber.

The objective of the hybridization of this rose variety was to create a new and distinct variety with unique qualities, such as:

1. Uniform and abundant pink flowers;
2. Vigorous, but compact growth when propagated on its own roots;
3. Exceptional disease resistance; and
4. Reduced apical dominance in flowering habit. The new variety consistently produces flowers evenly from the lower branches to the top of the plant.

This combination of qualities is not present in previously available commercial cultivars of the climbing class, known to the inventor, and distinguish 'Poulcy034' from all other varieties of which we are aware.

As part of the rose development program, Mogens N. Olesen germinated the seeds from the aforementioned hybridization during winter of 2006 and conducted evaluations on the resulting seedlings in a controlled environment in Fredensborg, Denmark. 'Poulcy034' was selected in the spring of 2007 by the inventor as a single plant from the progeny of the aforementioned hybridization.

Asexual reproduction of 'Poulcy034' by rooted cuttings was first done by Mogens N. Olesen in the nursery in Fredensborg, Denmark in July, 2007. This initial and other subsequent asexual propagations conducted in controlled environments have demonstrated that the characteristics of 'Poulcy034' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcy034'.

Specifically illustrated in FIG. 1 of the drawings are open flowers, petals detached, sepals, flower buds, receptacle, and reproductive flower parts.

Figure 1:
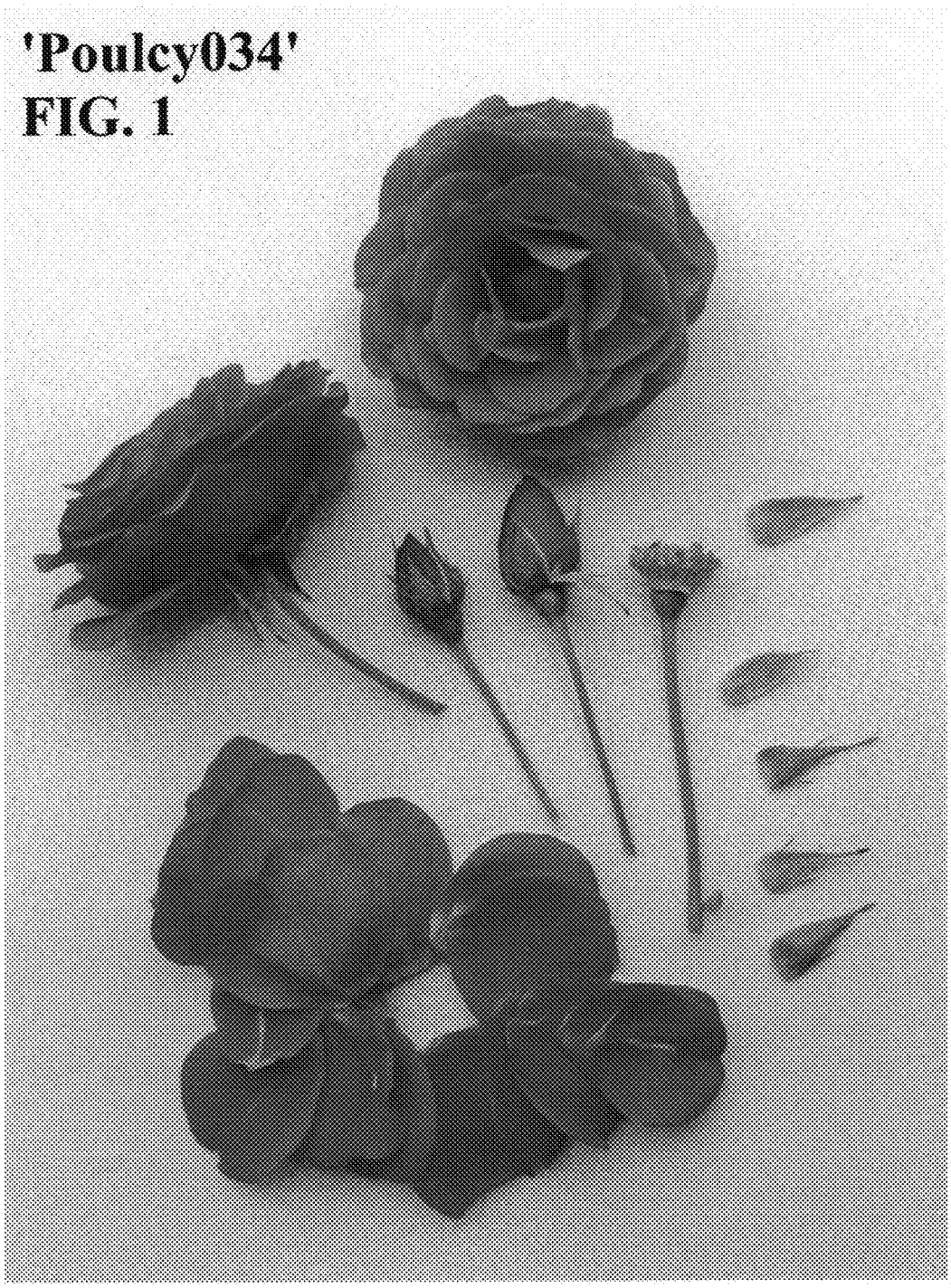
Figure 2:
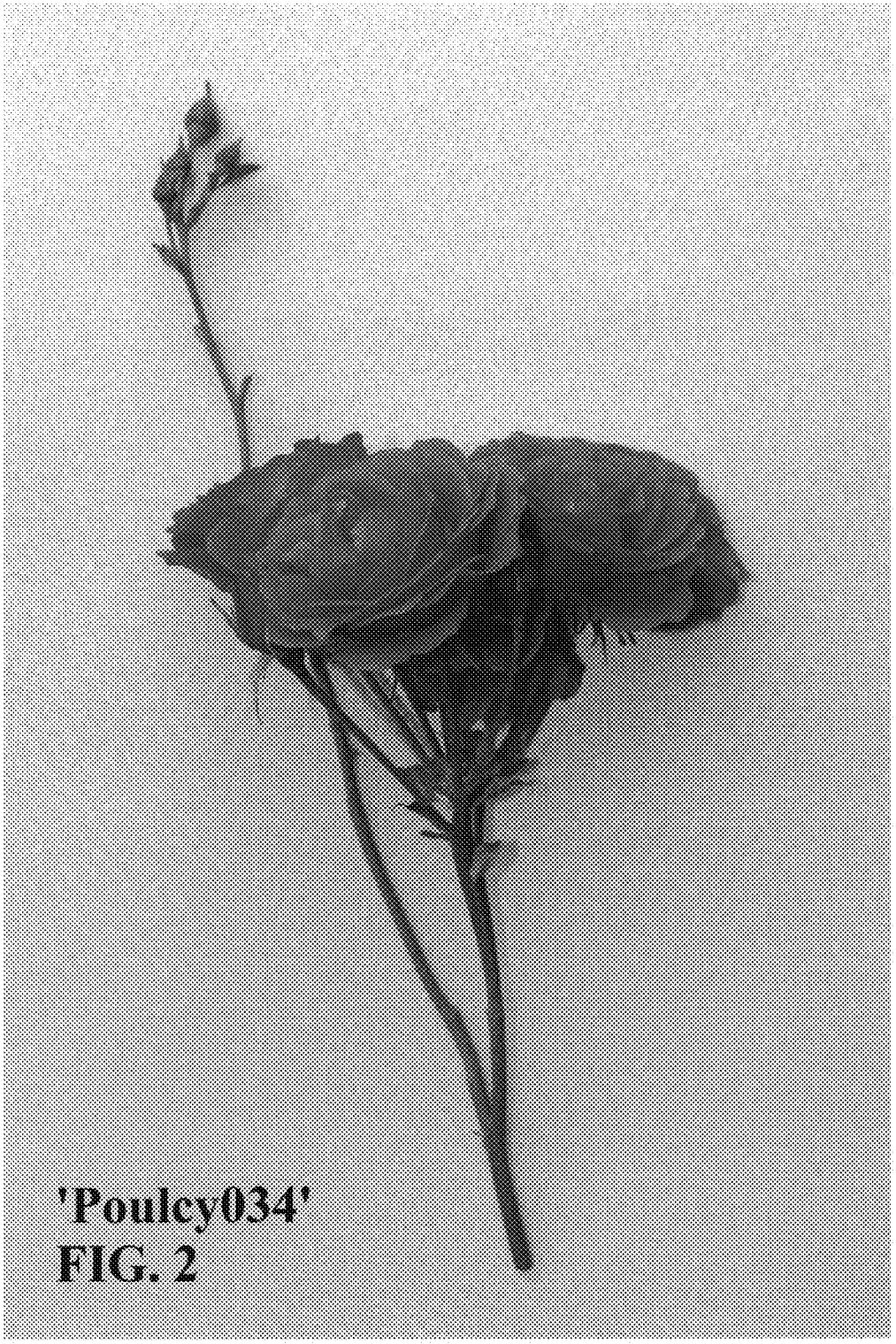

Specifically illustrated in FIG. 2 is a flowering branch.

Figure 3:
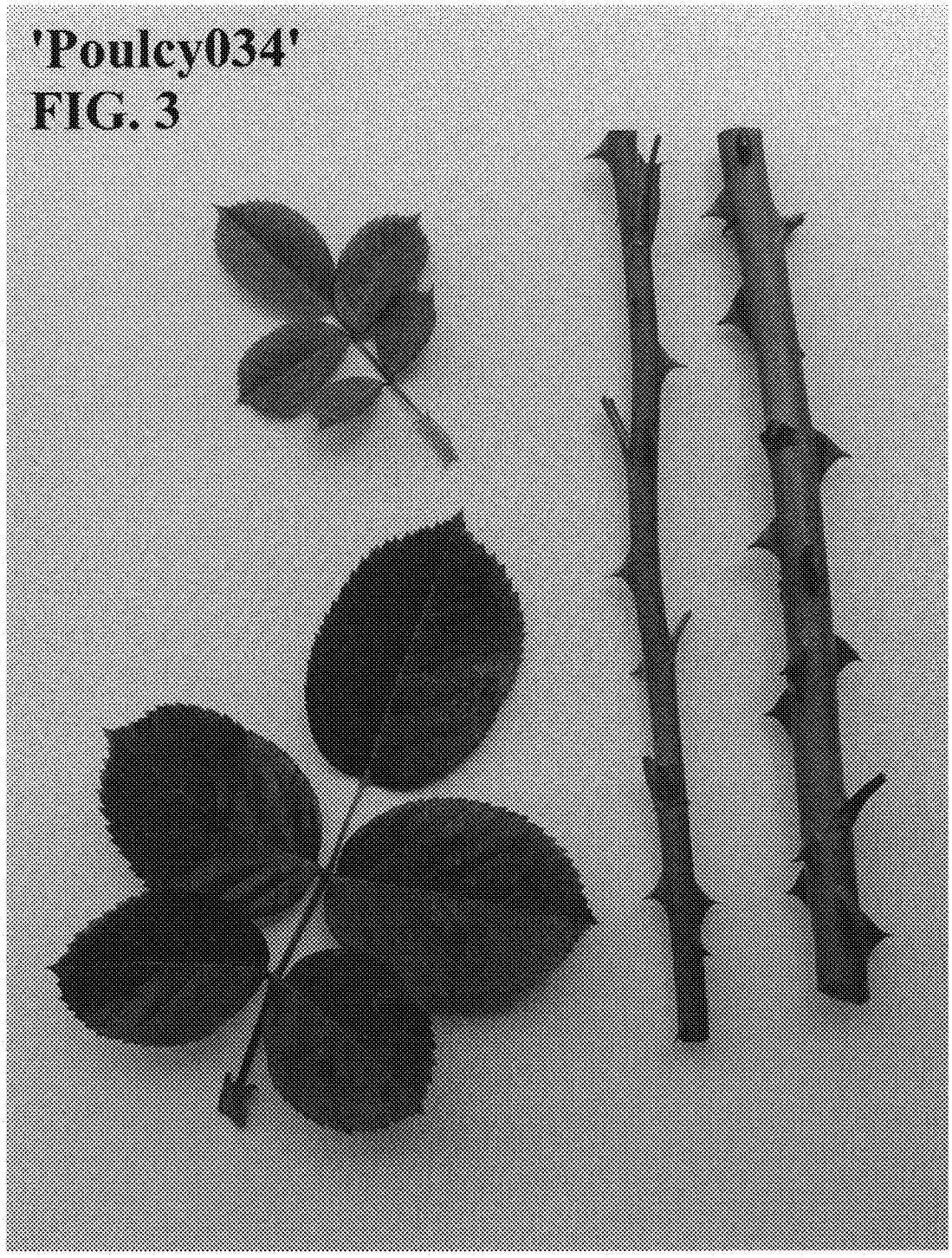

Specifically illustrated in FIG. 3 of the drawings are leaves and bare stems. Plants shown are 2 years of age.

DETAILED DESCRIPTION OF THE VARIETY

The following is a description of 'Poulcy034', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcy011' U.S. Plant Pat. No. 16,584 are compared to 'Poulcy034' in Chart 1.

CHART 1

| | 'Poulcy034' | 'Poulvam' |
|---|---|---|
| Petal Count | 28 | 60 |
| Flower Diameter | 85 mm | 45 to 55 mm |
| General Tonality of Flower Color | Red-Purple Group N57B | Red-Purple Group 62C to 62D with intonations of Red-Purple Group 58C at the center |

Flower and flower bud:

*Blooming habit*.—Continuous.

*Flower bud*.—Size: Upon opening, 30 mm in length from base of receptacle to end of bud. Bud diameter is 13 mm. Bud form: Ucerolate to ovoid. Bud color: As sepals divide petals are Red Group 53B. Sepal inner surface: Color: Yellow-Green Group 145A. Surface: Lightly pubescent. Sepal outer surface: Color: Yellow-Green Group 144A. Texture: Smooth. Sepal Shape: Apex: Cirrhose. Base: Flat at union with receptacle. Sepal Margin: Margins have weak foliaceous appendages on three of the five sepals. Sepal size: 27 mm long, 10 mm wide. Receptacle: Texture: Smooth. Size: 8 mm in height, 9 mm wide. Color: Yellow-Green Group 144A. Shape: Campanulate. Pedicel: Surface: Smooth. Length: 45 mm. Diameter: 2 mm on average. Color: Yellow-Green Group 144A. Strength: Strong. Peduncle: Length: 10 to 25 cm. Diameter: About 4 mm. Color: Yellow-Green Group 144A. Texture: Smooth.

*Flower bud development*.—Flower buds are borne in clusters of about 9 flower buds per stem. Development as a corymb. Reduced apical dominance in flower habit causes flower buds develop evenly from the base of the plant to the upper branches.

*Flower bloom*.—Fragrance: Honey perfumed scent. Duration: The blooms have a duration on the plant of approximately 10 days. Petals fall cleanly away from plant after flowers have fully matured. Size: Flower diameter is 85 mm when open. Flower depth is 33 mm. Flower shape: Rosette double flower with many slightly overlapping petals of different sizes. Shape of flower, side view: The upper portion is flat. The lower portion is flat.

*Petalage*.—Under normal conditions, flowers have about 28 petals.

*General tonality of flower*.—Open flowers are Red-Purple Group N57B.

*Petal color*.—Upon opening, outer petals Upper surface: Red-Purple Group N57B. Lower surface: Red-Purple Group 61B. Upon opening, inner petals: Upper surface: Red-Purple Group N57A. Lower surface: Red-Purple Group 58B. Basal petal spots, upon opening: Upper surface: Yellow Group 9B. Lower surface: Yellow Group 10D. After opening, outer petals Upper surface: Red-Purple Group N57B. Lower surface: Red-Purple Group N57C. After opening, inner petals: Upper surface: Red-Purple Group N57B. Lower surface: Red-Purple Group N57C. Basal petal spots, after opening: Upper surface; Yellow Group 10C. Lower surface: Yellow Group 10D.

*Petals*.—Petal Reflex: Weak. Margin: Entire and uniform with occasional cleft. Moderate undulations. Shape: Broad and elliptic. Apex shape: Rounded with occasional small point. Base shape: Obtuse. Size: 45 mm (l)×50 mm (w). Texture: Smooth. Thickness: Average.

*Petaloids*.—Size: 20 mm (l) by 10 mm (w). Quantity: About 4. Shape: Elliptical with an acute base and rounded apes. Color: Upper surface is Red-Purple Group N57, undersurface is Red-Purple Group N57B. At the base of the petaloid there is a spot of Yellow Group 10C.

*Reproductive flower parts*.—Pollen: None observed. Anthers: Size: 2 mm in length. Color: Yellow-Orange Group 17C. Quantity: 60 on average. Filaments: Color: Yellow Group 13B. Length: 5 mm. Pistils: Length: 4 mm. Quantity: 25 on average. Stigmas: Color: Orange-White Group 159A. Styles: Color: Red Group 52A. Location of stigmas: Inferior in location relative to the length of the filaments and the height of the anthers. Hips: None Observed.

Plant:

*Plant growth*.—Upright, bushy. Plants are 135 cm in height, and 90 cm wide.

*Stems*.—Color of juvenile growth: Yellow-Green Group 144B. Color of mature growth: Yellow-Green Group 144B. Length: Canes are about 50 cm from the base of the plant to the flowering portion. Diameter: About 10 mm. Internodes: On mature canes about 45 mm between nodes. Surface Texture: Young wood: Smooth. Older wood: Smooth.

*Long prickles*.—Incidence: 9 prickles per 10 cm of stem. Size: Average length of prickles on mature stems is 8 mm. Shape: Upper portion is convex. Lower portion is concave. Color: Juvenile prickles: Greyed-Orange Group 164B. Mature prickles: Greyed-Orange Group 164B with intonations of Greyed-Red Group 180B.

*Plant foliage*.—Compound leaf: 170 mm (l)×110 mm (w). Quantity: 2 leaves per 10 cm of stem on average. Leaf bearing angle to the stem: 45 degrees. Color of juvenile foliage: Upper side: Yellow-Green Group 144B with Greyed-Red Group 181A at margins. Lower side: Yellow-Green Group 144B with Greyed-Red Group 181A at margins. Color of mature foliage: Upper side: Yellow-Green Group 146A. Lower side: Yellow-Green Group 148B.

*Plant leaves and leaflets*.—Stipules: Size: 23 mm long, 3 mm wide. Quantity: 2 per compound leaf. Shape: Linear, slightly broad based with outward extending apices. Margins: Finely serrated. Color: Yellow-Green Group 144A. Petiole: Length: 40 mm. Diameter: 2 mm. Upper surface color: Yellow-Green Group 144A with intonations of Greyed-Purple Group 181A. Lower surface color: Yellow-Green Group 144B. Rachis: Length: 40 mm. Upper surface color: Yellow-Green Group 144A with intonations of Greyed-Purple Group 181A. Lower surface color: Yellow-Green Group 144B. Leaflet: Quantity: Normally 5 leaflets. Margins: Serrated. Size: Terminal leaflets are about 75 mm long, X 52 mm wide.

Shape: Generally elliptical. Base: Rounded. Apex: Acuminate. Texture: Smooth to somewhat rugose. Thickness: Average. Arrangement: Odd pinnate. Venation: Reticulate. Glossiness: Moderately glossy.

*Disease resistance*.—Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

*Cold hardiness*.—The variety is tolerant to USDA Cold Hardiness Zone 6.

*Heat tolerance*.—The variety has been found to be suitable for climate conditions found in the American Horticulture Society heat zone 7.

We claim:

1. A new and distinct variety of rose plant of the climbing rose class named 'Poulcy034', substantially as illustrated and described herein, due to its abundant pink flowers, disease resistance, and extended period of bloom.

* * * * *

'Poulcy034'

'Poulcy034'

'Poulcy034'